United States Patent
Otagiri et al.

(10) Patent No.: US 7,893,212 B2
(45) Date of Patent: Feb. 22, 2011

(54) S-NITROSO GROUP-CONTAINING ALBUMIN, METHOD FOR PRODUCTION, AND ANTICANCER AGENT

(75) Inventors: Masaki Otagiri, Kumamoto (JP); Keisuke Nakajo, Osaka (JP); Naohisa Katayama, Osaka (JP); Toshiya Kai, Osaka (JP)

(73) Assignee: Nipro Corporation, Osaka (JP)

( * ) Notice: Subject to any disclaimer, the term of this patent is extended or adjusted under 35 U.S.C. 154(b) by 39 days.

(21) Appl. No.: 12/201,825

(22) Filed: Aug. 29, 2008

(65) Prior Publication Data

US 2009/0099337 A1  Apr. 16, 2009

(30) Foreign Application Priority Data

Aug. 31, 2007  (JP) .............................. 2007-225839

(51) Int. Cl.
   *C07K 16/00* (2006.01)
(52) U.S. Cl. .................................................... 530/364
(58) Field of Classification Search ....................... None
    See application file for complete search history.

(56) References Cited

U.S. PATENT DOCUMENTS 6,291,424 B1  9/2001  Stamler et al.
2010/0222260 A1*  9/2010  Cabrales et al. ............... 514/12

OTHER PUBLICATIONS

Ewing et al., "Nitrosylated Bovine Serum Albumin Derivatives as Pharmacologically Active Nitric Oxide Congeners", The Journal of Pharmacology and Experimental Therapeutics, 1997, vol. 283, No. 2, pp. 947-954.*
Jakubowski, M., "Molecular basis of homocysteine toxicity in humans", Cellular and Molecular Life Sciences, 2004, vol. 61, pp. 470-487.*
Product Literature for "Traut's Reagent"—< www.piercenet.com/products/browse.cfm?fldID=02040121 >—Jul. 5, 1010.*
Sigma Product Literature for 2-Iminothiolane. No date.*
Singh et al. "Formation of N-Substituted 2-Iminothiolanes When Amino Groups in Proteins and Peptides Are Modified by 2-Iminothiolane", Analytical Biochemistry, 1996, vol. 236, pp. 114-125.*
Naohisa Katayama, et al., "Design and Evaluation of S-Nitrosylated Human Serum Albumin as a Novel Anticancer Drug", The Journal of Pharmacology and Experimental Therapeutics, vol. 325, No. 1, pp. 69-76, Apr. 2008.
Hidemasa Katsumi, et al., "Physicochemical, Tissue Distribution, and Vasodilation Characteristics of Nitrosated Serum Albumin: Delivery of Nitric Oxide in Vivo", Journal of Pharmaceutical Sciences, vol. 93, No. 9, pp. 2343-2352, Sep. 2004.
Hidemasa Katsumi, et al. "Development of Polyethylene Glycol-Conjugated Poly-S-Nitrosated Serum Albumin, a Novel S-Nitrosothiol for Prolonged Delivery of Nitric Oxide in the Blood Circulation in Vivo", The Journal of Pharmacology and Experimental Therapeutics, vol. 314, No. 3, pp. 1117-1124, Sep. 2005.
Angelika M. Burger, et al., "Pre-Clinical Evaluation of a Methotrexate-Albumin Conjugate (MTX-HSA) in Human Tumor Xenografts in Vivo", International Journal of Cancer, vol. 92, pp. 718-724, Jan. 1, 2001.
F. Fabbri, et al., "Pro-Apoptotic Effect of a Nitric Oxide-Donating NSAID, NCX 4040, on Bladder Carcinoma Cells", Apoptosis, vol. 10, No. 5, pp. 1095-1103, Oct. 1, 2005.
Tanyel Kiziltepe et al., "JS-K, a GST-Activated Nitric Oxide Generator, Induces DNA Double -Strand Breaks, Activates DNA Damage Response Pathways, and Induces Apoptosis in Vitro and in Vivo in Human Multiple Myeloma Cells", Blood, vol. 110, No. 2, pp. 709-718, Jul. 2007.
Basil Rigas et al., "Nitric-oxide-donating NSAIDs as agents for cancer prevention", Trends in Molecular Medicine, Jul. 2004, pp. 324-330, vol. 10, No. 7.
Seth Hallström et al., "S-Nitroso Human Serum Albumin Treatment Reduces Ischemia/Reperfusion Injury in Skeletal Muscle via Nitric Oxide Release", Circulation 2002, pp. 3032-3038, vol. 105.
Yu Ishima et al., "S-Nitrosylation of Human Variant Albumin Liprizzi (R410C) Confers Potent Antibacterial and Cytoprotective Properties", The Journal of Pharmacology and Experimental Therapeutics, 2007, pp. 969-977, vol. 320, No. 3.

* cited by examiner

*Primary Examiner*—Suzanne M. Noakes
(74) *Attorney, Agent, or Firm*—Sughrue Mion, PLLC

(57) ABSTRACT

The present invention provides an S-nitroso group-containing albumin, comprising an S-nitroso group introduced to at least one lysine in the amino acid sequence for albumin. The S-nitro group has been introduced into a lysine in the S-nitroso group-containing albumin of the invention to allow more S-nitroso groups to be included in the albumin, thus ensuring more potent inhibition of cancer cells in NO groups.

1 Claim, 2 Drawing Sheets

SEQUENCE LISTING

```
<160> NUMBER OF SEQ ID NOS: 1

<210> SEQ ID NO 1
<211> LENGTH: 585
<212> TYPE: PRT
<213> ORGANISM: Homo sapien
<220> FEATURE:
<223> OTHER INFORMATION: Albumin

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

```
Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
```

```
                                       -continued
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

S-NITROSO GROUP-CONTAINING ALBUMIN, METHOD FOR PRODUCTION, AND ANTICANCER AGENT

BACKGROUND OF THE INVENTION

1. Field of the Invention

The present invention relates to an S-nitroso group-containing albumin, a method for preparing the same, and an anticancer agent, and more specifically relates to an S-nitroso group-containing that is an endogenous substance with low potential for adverse effects, a method for preparing the same, and an anticancer agent.

2. Background Information

Nitric oxide (NO) is known to function as a mediator not only in transmitting information in the circulatory system and nervous systems but also in infection, inflammation, and immune response, and to furthermore be involved in a broad range of vial phenomena, such as carcinogenesis and the regulation of apoptosis.

NO also undergoes oxidation in response to the surrounding environment and produces a variety of reactive nitrogen oxides, which may bring about both physiological and pathophysiological activities.

NO has beneficial antioxidant action and anti-apoptosis action, and the administration of NO during organ transplants and ischemic disease has therefore been studied, resulting in therapeutic efficacy.

On the other hand, NO is also known to have harmful effect such as effect in stimulating apoptosis and cytotoxic effect, and recent research on the application of such qualities in cancer chemotherapy has been actively underway.

What have been studied most often thus far are NO-NSAIDs, in which NO and nonsteroidal anti-inflammatories (NSAIDs) are chemically bonded by a spacer molecule. The NO-NSAIDs are known to induce a variety of in vitro cellular phenomena in cancer cells, such as inhibition of Wnt signaling, activation of NF-κB, inhibition of NO synthase, inhibition of MAPK signaling, and induction of cyclooxygenase 2.

In vivo oncotherapeutic efficacy has also been reported in cancer animal models (see Rigas B et al. Trends Mol Med. 2004, 10, 324-330).

It has also become evident that proteins such as albumin serve as endogenous NO reservoirs, and are involved in regulating NO concentrations in the living body. Research on the effects of S-nitroso-albumin as NO substitution therapy to address decreased endogenous NO production during organ transplants and ischemi disease have studied, and therapeutic efficacy in neointimal thickening and the like associated with suppressed platelet deposition, balloon disorder, and ischemic-reperfusion disorder have been revealed (see Hallstrom S et al. Circulation. 2002, 105, 3032-3038, and Ishima Y et al. J Pharmacol Exp Ther. 2007, 320, 969-977).

However, no examples of research on S-nitroso-albumin for cancer have been reported until now.

SUMMARY OF THE INVENTION

An object of the present invention is to provide an S-nitroso group-containing albumin, as well as a method for preparing the same and an anticancer agent in order to obtain a highly efficiency and safety anticancer agent by using a toxic action of NO and by combining the action with an action of albumin, which is an endogenous substance, in the living body, so as to advance research on applications in cancer chemotherapy that have not yet been researched.

The present invention provides an S-nitroso group-containing albumin, comprising an S-nitroso group introduced to at least one lysine in the amino acid sequence for albumin.

Also, the present invention provides an anticancer agent comprising S-nitroso group-containing albumin.

Further, the present invention provides a method for preparing a S-nitroso group-containing albumin, comprising the steps of introducing a thiol group to at least one amino acid in the amino acid sequence for albumin, and nitrosolating the thiol group.

An S-nitro group has been introduced into a lysine in the S-nitroso group-containing albumin of the invention to allow more S-nitroso groups to be included in the albumin, thus ensuring more potent inhibition of cancer cells in NO groups.

The anticancer agent of the invention is also based on endogenous albumen which is already present in the living body, thus allowing an anti-cancer agent with low potential for adverse effects to be provided.

Furthermore, the method for preparing the S-nitroso group-containing albumin of the invention allows the reaction conditions and the like to be adjusted as needed, allowing S-nitroso groups to be readily introduced into amino acids, the number of S-nitroso groups introduced to be controlled, and a good balance to be achieved between cancer cell-inhibiting effects and adverse effects.

DETAILED DESCRIPTION OF THE PREFERRED EMBODIMENTS

Figure 1:
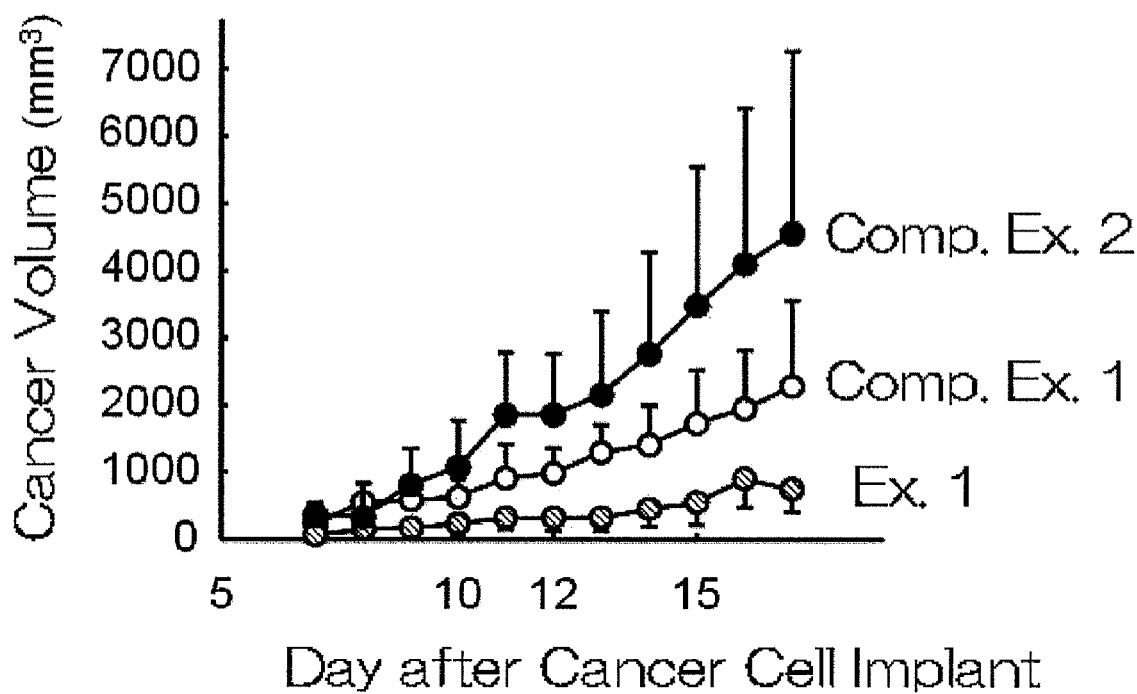
FIG. 1 is a graph of the changes in cancer volume over time after cancer cell implant (Test Example 1).

An S-nitro group-containing albumin of the invention is an albumin introduced at least one, two or more, preferably three or more S-nitroso group.

An anti-cancer agent of the invention is formulated with the S-nitro group-containing albumin.

The albumin used in the invention may be a naturally derived albumin or an albumin produced by recombinant techniques.

The naturally derived albumin means a protein which is widely distributed in blood, intercellular fluid and the like in the human body. The albumin may be a protein derived from a mammal other than human such as monkey, cow, sheep, goat, horse, pig, rabbit, dog, cat, mouse, rat, and the like. Not only serum albumin of blood and intercellular fluid, but also egg albumin, myoalbumin (myogen), and the like may be used. Such natural albumin has, for example, the amino acid sequence of SEQ. ID No. 1.

Albumin produced by recombinant techniques means albumin consisting of the amino acid sequence of SEQ. ID. No. 1, with one or more amino acid substitutions, deletions, insertions, and/or additions, as long as it has the same function as natural albumin, that is, as long as it has the function of maintaining normal osmotic pressure in the blood stream and maintaining fluid levels in the blood, and/or the secondary structure of the albumin is not modified. The number of amino acid substitutions, deletions, insertions, and/or additions may be 1 to about 10, for example.

Included in particular are proteins in which one or more amino acids in the amino acid sequence of SEQ. ID. No. 1 are substituted by other amino acids in order to increase the number of S-nitroso groups that are introduced. Examples of albumin that are known to have the function of maintaining normal osmotic pressure in the blood stream and maintaining fluid levels in the blood as described above, despite the substitution of one or more amino acids by other amino acids, include an albumin obtained by the cysteine substitution of the 410-arginine in the amino acid sequence of SEQ. ID. No. 1.

The S-nitroso group-containing albumin means a protein in which a nitroso group has been substituted for an amino acid constituting the albumin, particularly a sulfur atom present in the amino acids, such as the sulfur atom in a thiol group. The thiol group may be either one in cysteine, cystine, or methionine, or any that has been introduced into amino acid residues other than those.

There are usually 35 cysteine residues in natural albumin, of which 34 form disulfide bonds for the formation of the secondary structure of the albumin. The S-nitroso group-containing albumin would thus have the S-nitroso group introduced into only one cysteine. Albumin produced by a recombinant technique would also basically have the S-nitroso group introduced into the one cysteine.

Examples of methods for introducing a thiol group into at least one amino acid in the amino acid sequence constituting albumin, that is, methods for introducing a thiol group into amino acid residues other than cysteine, cystine, or methionine, include methods commonly known in the field.

A preferable method, for example, is the use of a thiol reagent (such as 2-iminothiolane or a salt thereof) to introduce a thiol group to the $\epsilon$-amino group of lysine. Other examples include methods for introducing compounds with amino groups and thiol groups (such as 2-aminoethanethiol) into the carboxylic acid residue of glutamic acid by means of an aminolysis reaction, and methods for introducing compounds with carboxylic acids and thiol groups (such as 2-carboxyethanethol) into the $\epsilon$-amino group of lysine by means of an aminolysis reaction.

The desired number of thiol groups can be introduced into the $\epsilon$-amino group of lysine present in the albumin by controlling the thiolation reaction, such as the albumin-thiol reagent molar ratio, reaction time, and reaction temperature, for example. Examples of the albumin:thiol reagent molar ratio include about 1:5 to about 1:200, and about 1:10 to about 1:100. The reaction time is about 1 min to about 10 hours, and preferably about 10 min to about 2 hours. The reaction temperature is preferably about room temperature, for example.

The method for substituting an S-nitroso group for a thiol group that has been introduced or that is intrinsic to the albumin is not particularly limited, and can be any method known in the relevant field. Examples include methods involving the use of a nitrosolating reagent (specifically, nitrite ions, isoamyl nitrite, n-butyl nitrite, etc.). The use of isoamyl nitrite or n-butyl nitrite is industrially preferred in view of the ability to bring about synthesis under relatively moderate conditions. The desired number of nitroso groups can be introduced into any thiol groups present in the albumin by adjusting the nitrosolation reaction, such as the albumin and nitrosoolating reagent molar ratio, the reaction time, and the reaction temperatures. Examples of the albumin:nitrosolating reagent molar ratio include about 1:0.1 to about 1:200, and about 1:0.5 to about 1:70. The reaction time is about 1 min to about 20 hours, and preferably about 10 min to about 3 hours. The reaction temperature is preferably about room temperature, for example.

Thiol groups are also preferably reduced prior to the reaction. Thiol groups can be reduced, for example, using 1,4-dithiothreitol or the like.

During proteins are produced from transformants when the production of albumin by recombinant techniques, S-nitroso group-containing albumin can be produced by substituting the essential amino acid with an amino acid derivative into which a thiol group has been introduced and/or an S-nitroso group-containing amino acid derivative as the nutrient source amino acid.

At least one S-nitroso group is introduced per albumin molecule, but 2 or more, 4 or more, and even 6 or more are preferred. For example, about 5 to 7 S-nitroso groups can be introduced when, under the conditions in Example 1 below, 2-iminothiolane is used to introduce a thiol group into the $\epsilon$-amino group of lysine in recombinant albumin having the amino acid sequence shown in SEQ. ID. No. 1, and nitrite ions are used to bring about S-nitrosolation.

The anti-cancer agent of the invention includes the above S-nitroso group-containing albumin as an active ingredient.

The S-nitroso group-containing albumin may be used without modification as the anti-cancer agent but usually is preferably formulated using pharmaceutically and pharmacologically acceptable additives, excipients, and the like.

The route by which the anti-cancer agent is administered is not particularly limited. Examples include any route of administration such as intradermal, subcutaneous, intramuscular, intraperitoneal, transdermal, transmucosal, oral, inhalation administration, and the like, although parenteral routes of administration, especially administration by injection, are preferred.

The dosage form of the medicinal composition of the invention can be any that is suitable for administration by the above routes of administration, such as injections, patches, cataplasms, ophthalmic solutions, nasal solutions, sprays, tablets, capsules, lozenges, sublingual tablets, creams, lotions, and powders. It may also be encapsulated in biodegradable liposomes, microcapsules, or microspheres, and may also be formulated in lyophilized form.

Particularly in the case of injections, the S-nitroso group-containing albumin may be in the form of a solution or suspension. Additives commonly used in the field, such as pH regulators, electrolytes, saccharides, vitamins, pharmacologically acceptable salts or fatty acids and/or amino acids, may be added as needed.

For solutions and suspensions, any solution stipulated in the Japanese Pharmacopoeia, for example, can be used. Water (water for injection), normal saline, and various types of buffers (such as phosphate buffer) can primarily be used.

pH regulators commonly used in injection should be used. Examples include organic acids such as citric acid, tartaric acid, acetic acid, and lactic acid; inorganic acids such as hydrochloric acid and phosphoric acid; and inorganic bases such as sodium bicarbonate, sodium carbonate, and sodium hydroxide.

A variety of water-soluble salts conventionally used in infusions can be used as the electrolytes. Examples include various inorganic (for example, sodium, potassium, calcium, magnesium, phosphorus an eth elike) water-soluble salts (for example, chloride, sulfate, acetate, gluconate, lactate and the like) that are considered necessary in terms of maintaining bodily functions or the humoral electrolyte balance.

A variety of saccharides conventionally used in infusions can be used. Glucose is an example. Examples include monosaccharides such as glucose, fructose, galactose; disaccharides such as lactose, maltose; polyols such as glycerol;

sugar alcohols such as xylitol, sorbitol, mannitol; Dexetrines such as Dexetrine 40 or Dexetrine 80; sucrose, and the like.

Various conventionally used water-soluble/liposoluble vitamins can be used. Examples include Vitamin A, provitamin A, vitamin D, provitamin D, vitamin E, vitamin K, vitamin B1, vitamin B2, niacin, vitamin B6 groups, pantothenic acid, biotin, Mio-inositol, Colin, folic acid, vitamin B12, vitamin C, vitamin P, vitamins U, and the like.

Examples of pharmacologically acceptable salts or fatty acids include alkali metals such as sodium, potassium; alkaline-earth metals such as calcium and magnesium; organic acid such as formic acid, acetic acid, oxalic acid, tartaric acid, maleic acid, citric acid, caprylic acid, succinic acid and malic acid; organic bases such as trimethylamine, triethylamine, pyridine, picoline, ethanolamine, diethanolamine, triethanolamine and dicyclohexylamine.

Examples of amino acids include, for example, alanine, arginine, asparagine, aspartic acid, cysteine, glutamine, glutaminic acid, glycine, histidine, hydroxyproline, isoleucine, leucin, lysin, methionine, phenylalanine, proline, serine, threonine, tryptophan, tylosin and valine. In addition, amino acid derivatives such as N-acetyl methionine may also be used.

Injections can be manufactured in accordance with the usual pharmaceutical procedures. That is, the injections containing the S-nitroso group-containing albumin of the invention can be prepared through dilution and/or dissolution to a final S-nitroso group-containing albumin concentration of between about 10 mg/mL and about 150 mg/mL, and a pH of about 4.5 to about 8.7 using various types of buffers, common commercially available infusions (such as amino acid infusions and electrolyte infusions) or aqueous solutions containing ingredients similar to these, and the like.

The S-nitroso group-containing albumin per unit is not particularly limited, but may be, for example, prepared in the form of an injection containing about 1 to about 1000 mg, and preferably about 10 to about 100 mg.

When the anti-cancer agent of the invention is thus administered into the body, the potential for adverse effects can be further reduced, and the S-nitroso groups can be more stable, because the agent is based on endogenous albumin. The S-Nitroso group containing albumin is also a high-molecular substance and can thus be expected to result in EPR effects (enhanced permeation and retention effects) permitting the drug to be delivered more effectively and in greater concentrations to cancerous tissue.

EXAMPLE 1

The anti-cancer agent of the invention was produced by the following procedures.

20 mL normal saline aqueous solution of 25% (w/v) recombinant human serum albumin (provided by KK Baifa, SEQ. ID. No. 1) was mixed to a concentration of 0.5 mM in 480 mL of 0.1 M potassium phosphate solution (pH 7.8) containing diethylene triaminepentaacetic acid. 206.45 mg 2-iminothiolane hydrochloride was added, and a reaction was brought about for 1 hour at room temperature.

1 mL of isopentyl nitrite was then added, and a reaction was brought about for 3 hours. The reaction solution was concentrated, and the solvent was replaced with normal saline.

Quantification of a protein and NO revealed that about six (N=3) S-nitroso groups were introduced per albumin molecule.

A normal saline solution with the albumin concentration of 1 mM was then prepared, and an anti-cancer agent of the invention was prepared by sterilization filtration.

Comparative Example 1

A Recombinant Human Serum Albumin Solution

A normal saline aqueous solution (100 μM) of the recombinant human serum albumin (provided by KK Baifa, SEQ. ID. No. 1) was prepared as a comparison with the anti-cancer agent of the invention for using Test Examples 1 to 3 described below.

Comparative Example 2

A Normal Saline

A normal saline was prepared as a comparison with the anti-cancer agent of the invention for using Test Example 1 described below.

Comparative Example 3

A Phosphate Buffer Solution

A phosphate buffer solution was prepared as a comparison with the anti-cancer agent of the invention for using Test Example 3 described below.

Test Example 1

$10^6$ C26 cells which is cancer cells derived from mouse colon cancer (provided by Institute of Development, Aging, and Cancer, Tohoku University) were subcutaneously transplanted to the dorsal region of Balb/c mice to produce a mouse model of cancer.

A solution of S-nitroso group-containing albumin (Example 1) was intravenously administered for 10 consecutive days at a dose of 10 μmol/kg 3 days after the cancer cell transplant.

The recombinant human serum albumin solution (Comparative Example 1) and normal saline (Comparative Example 2) were similar administered intravenously as controls.

FIG. 1 is a graph of the changes in tumor volume over time after cancer cell implant.

The major axis (a) and minor axis (b) of the tumors were measured using calipers, and calculated cancer volume as $0.4 \times a \times b^2$.

The results in FIG. 1 show that the S-nitroso group-containing albumin of the invention significantly inhibited cancer hyperplasia compared to the normal saline group and albumin group.

Test Example 2

The effects of the S-nitroso group-containing albumin of the invention in inhibiting the hyperplasia of C26 cells were evaluated. Specifically, a C26 cell suspension ($1 \times 10^5$ cells/mL RPMI-1640 culture (10% FCS)) was prepared, and the cell suspension was used to inoculate 96-well plates ($1 \times 10^4$ cell/well) for 32 hours of incubation in a $CO_2$ incubator. S-nitroso group-containing albumin was further added. Here, the S-nitroso group-containing albumin was added in three concentrations of 25, 50, or 100 μM. Recombinant human serum albumin (Comparative Example 1) was used as the control.

After 48 hours of incubation, Cell Counting Kit-8 solution (WST-8) was added, and the absorbance at 450 nm was determined using a microplate reader after 2 hours of incubation at 37° C.

Figure 2:
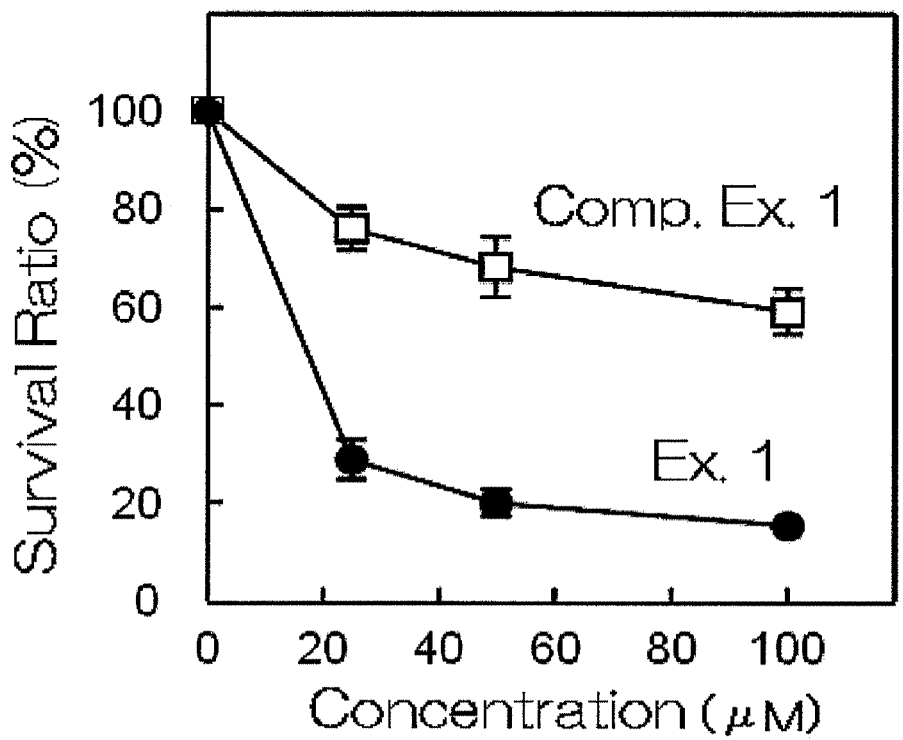
FIG. 2 is a graph of the changes in cancer survival ratio over albumin concentration (Test Example 2).

The results are given in FIG. 2.

The results in FIG. 2 show that the anti-cancer agent of the invention resulted in dose-dependent inhibition of the hyperplasia of C26 cells compared to the recombinant human serum albumin solution (Comparative Example 1).

Test Example 3

The apoptosis-inducing action of the S-nitroso group-containing albumin of the invention was evaluated. Specifically, the C26 cell suspension ($1\times10^5$ cells/mL RPMI-1640 culture (10% FCS)) was prepared, and the cell suspension was used to inoculate 96-well plates ($1\times10^6$ cell/well) for 12 hours of incubation in a $CO_2$ incubator. S-nitroso group-containing albumin was further added. Here, the S-nitroso group-containing albumin was added in three concentrations of 25, 50, or 100 μM. Recombinant human serum albumin (Comparative Example 1) and phosphate buffer solution were used as controls.

After 24 hours of incubation, the cells were treated with trypsin, were recovered, and were centrifuged for 5 min at 4000 rpm. A supernatant was removed. 200 μL PBS was added to the cell pellet for resuspension, followed by 10 min of centrifugation at 4000 rpm and the removal of the supernatant. The cells were stirred with the addition of 20 μL cell lysing buffer solution, were allowed to stand for 10 min at 4° C., and were centrifuged for 5 min at 15,000 rpm. The supernatant was recovered, 1 μL of RNase A solution was added, the mixture was incubated for 30 min at 50° C., another 1 μL proteinase K was added, and the mixture was incubated for 1 hour at 50° C. The extracted DNA was electrophoresed on 1% agarose gel.

Figure 3:
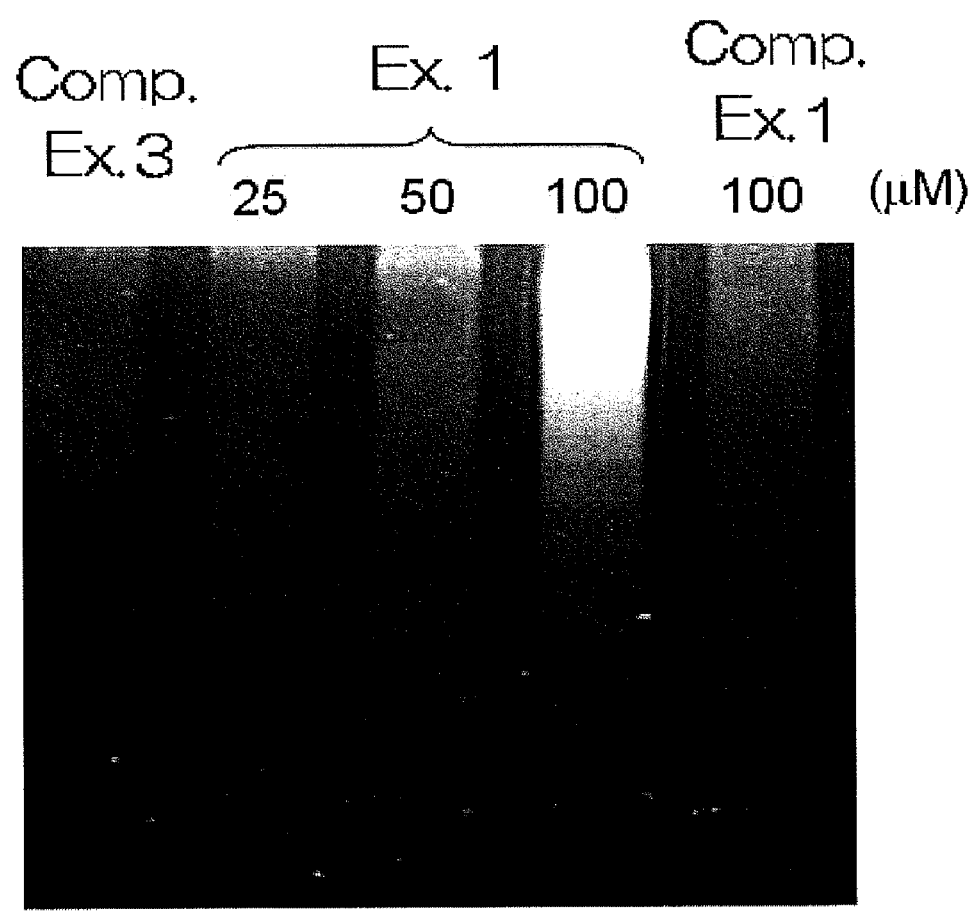
FIG. 3 is an electropherogram showing the result of Test Example 3.

The results are given in FIG. 3.

The results in FIG. 3 show that the S-nitroso group-containing albumin of the invention (Example 1) induced DNA fragments in C26 cells at high concentrations, thus suggesting that the S-nitroso group-containing albumin of the invention resulted in anti-cancer effects through the induction of apoptosis in cancer cells.

The S-nitroso group-containing albumin and anti-cancer agent of the invention are composed primarily of a substance based on an endogenous system referred to as S-nitroso group-containing albumin, thus allowing lower potential for adverse effects to be expected. Because the S-nitroso group-containing albumin is based on an endogenous substance, the nitroso groups can be expected to be more stable when administered to the body. EPR effects can furthermore be anticipated because the S-nitroso group-containing albumin, which is the technical product, is a high-molecular substance.

This application claims priority to Japanese Patent Application No. 2007-225839. The entire disclosure of Japanese Patent Application No. 2007-225839 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A method for preparing a S-nitroso group-containing albumin comprising the steps of introducing a thiol group to at least one lysine in the amino acid sequence for albumin by reacting an albumin with 2-iminothiolane and nitrosolating the thiol group.

* * * * *